United States Patent [19]

Kardys

[11] 3,932,634

[45] Jan. 13, 1976

[54] HIGH POTENCY VITAMIN WATER DISPERSIBLE FORMULATIONS

[75] Inventor: Joseph A. Kardys, Groton, Conn.

[73] Assignee: Pfizer Inc., New York, N.Y.

[22] Filed: Dec. 10, 1974

[21] Appl. No.: 531,332

Related U.S. Application Data

[63] Continuation of Ser. No. 374,488, June 28, 1973, abandoned, which is a continuation-in-part of Ser. No. 119,362, Feb. 26, 1971, abandoned.

[52] U.S. Cl. .................. 424/237; 424/284; 424/344
[51] Int. Cl.² ........................................ A61K 31/595
[58] Field of Search ........... 424/181, 227, 236, 237, 424/284, 344

[56] References Cited

UNITED STATES PATENTS

| | | | |
|---|---|---|---|
| 3,036,957 | 5/1962 | Lehman | 424/237 |
| 3,105,793 | 10/1963 | Lobel | 424/181 |
| 3,149,037 | 9/1964 | Aiello et al. | 424/236 |
| 3,244,595 | 4/1966 | Feigh | 424/237 |
| 3,253,992 | 5/1966 | Brooks | 424/237 |
| 3,359,167 | 12/1967 | Timreck | 424/344 |

OTHER PUBLICATIONS

Veterinary Drug Encyclopedia, (VDE), 1962, p. 195.
Chemical Abstracts, 71:53539e.

*Primary Examiner*—Norman A. Drezin
*Attorney, Agent, or Firm*—Connolly and Hutz

[57] ABSTRACT

A pharmaceutical composition consisting essentially of from about 25% to about 55% by weight of at least one oil-soluble vitamin in water together with from about 50% to about 85% of the total composition as a dispersing agent a mixture of polyoxyethylene sorbitan monooleate and an ester selected from polyethylene glycol 400 monooleate, decaglycerol dioleate, and decaglycerol tetraoleate.

2 Claims, No Drawings

HIGH POTENCY VITAMIN WATER DISPERSIBLE FORMULATIONS

CROSS REFERENCE TO RELATED APPLICATIONS

This application is a continuation of application Ser. No. 374,488 filed June 28, 1973 now abandoned which is a continuation in part of application Ser. No. 119,362 filed February 26, 1971 and now abandoned.

BACKGROUND OF THE INVENTION

This invention relates to certain novel vitamin compositions and more particularly, to non-aqueous, stable, readily water-dispersible vitamin compositions which contain more than one dispersing agent therein. The vitamins of this invention are oil-soluble vitamins such as vitamin A, vitamin $D_2$, vitamin E, or combinations thereof.

In general, the pharmaceutical art has long been concerned with the problem of finding a suitable way to render lipoid-soluble vitamins dispersible in aqueous media. For instance, although vitamin A palmitate of commerce is soluble in most common organic solvents and readily miscible in all proportions with ordinary mineral and vegetable oils, it is insoluble in water, thereby necessitating the use of an emulsifier or dispersing agent in this connection, i.e., when aqueous systems are desired. Since then, it has been found possible by other workers in the field to prepare clear aqueous dispersion of said vitamin in concentrations of up to about 100,000 U.S.P. units per gram by using polyoxyethylene derivatives of certain high molecular weight fatty acid esters such as the sorbitan fatty acid ester derivatives, for example, which act as dispersing agents for this purpose. Although this represented a great advance in the art at the time, the relatively long period required in order to effect said dispersion still remained a problem, which, in turn, necessitated special handling, etc. (e.g., the use of elevated temperatures, and the like).

It is, therefore, a primary object of the present invention to provide a non-aqueous, but yet rapidly water-dispersible vitamin composition of high potency which will, at the same time, remain stable under normal or ordinary conditions of use. Other objects and advantages of the present invention will be apparent to those skilled in the art from the description which follows herein.

SUMMARY OF THE INVENTION

In accordance with the present invention, the foregoing objects have now all been achieved by the discovery that up to 55% by weight of at least one oil soluble vitamin in water can be rapidly dispersed when mixed with from about 35% to about 85%, by weight of the total composition, of a dispersing agent consisting essentially of a mixture of polyoxyethylene sorbitan monooleate and an ester selected from polyethylene glycol 400 monooleate, decaglycerol dioleate, and decaglycerol tetraoleate. The vitamin composition is especially preferred which contains from 25 to 50% of at least one oil soluble vitamin selected from vitamin A, vitamin $D_2$, vitamin $D_3$, vitamin E, or combinations thereof. The ratio of said polyoxyethylene sorbitan monooleate to said ester may be from about 1:3 to about 3:1 by weight, and a ratio of from about 1:2 to about 2:1 is especially preferred. A composition also containing an antibiotic, especially oxytetracycline or neomycin, is also preferred.

The advantages afforded by the compositions of the invention are manifold: for instance, (a) they are rapidly dispersed in water, as aforesaid, in a matter of seconds to give clear, stable solutions of vitamins of high potency; (b) the component ingredients are all safe and effective for human use and (c) the compositions themselves find further application in the form of soft gelatin capsules, multivitaminaceous aqueous dispersions and/or other liquid vitamin preparations, such as syrups, elixirs, and the like, in combination with the watersoluble vitamins.

DETAILED DESCRIPTION OF THE INVENTION

In connection with a more detailed consideration of this invention, the oil-soluble vitamin component of the present compositions may be vitamin A, vitamin $D_2$, vitamin $D_3$, vitamin E, or combinations thereof. Vitamin A higher fatty acid esters are a particularly appropriate form of vitamin A, such as esters having at least eight carbon atoms in the acyl moiety of the ester grouping. Preferred esters for these purposes include pure vitamin A palmitate, vitamin A corn oil fatty acid esters and vitamin A coconut oil fatty acid esters. As previously indicated, the vitamin component is generally present in said compositions at a concentration level of up to about 55% by weight of the total. A preferred range in this respect would be from between about 15% and about 50% by weight of the total, for example, and an especially preferred range is from 25 to 50%. Needless to say, there is no real lower limit to the minimum concentration of oil-soluble vitamins that can be incorporated into these compositions, but it should be noted that concentrations above 15% represent the area in which the prior art has failed to provide satisfactory compositions. Where antibiotic is also incorporated in the composition, the difficulties have been even greater.

As an oil-soluble vitamin, alone or in combination with vitamin A or other oil-soluble vitamins in the present compositions, there may be used vitamin $D_2$ and/or $D_3$ preferably in the crystalline form or as high potency resin concentrate. Preferably the vitamin $D_2$ or $D_3$ resin concentrate is above 4,000,000 units per gram. The vitamin is generally present in a multi-vitamin composition at a concentration of 1% to 30% by weight depending on the potency of the vitamin concentrate.

The source of vitamin E activity may be a synthetic concentrate or a processed high potency natural tocopherol concentrate. The vitamin E content is generally present in a multi-vitamin composition at a concentration level of 10% to 55% by weight.

The polyoxyethylene derivative of the sorbitan monoester of this combination is desirably a polyethylene oxide derivative of such sorbitan fatty acid esters as sorbitan monopalmitate, sorbitan monooleate, sorbitan monostearate, etc. These compounds are all available commercially under various trademark names (e.g., the "Tween" trademark name of the Atlas Powder Company). Polyoxyethylene (20) sorbitan monooleate (Tween 80), which has twenty oxyethylene units per molecule, is especially preferred. The component so described can be present in said vitamin compositions at concentration levels ranging as high as 50% by weight of the total, and within the aforestated weight ratio range of about 1:3 to about 3:1, with respect to the ester component.

The third principal component of these compositions, viz., the polyethylene glycol 400 monooleate, decaglycerol dioleate, or decaglycerol tetraoleate, is generally present to the extent that it is no more than 50% by weight of the total vitamin composition and at such a level that it falls within the above indicated weight ratio range. It is the last named component of the mixture that actually renders the present compositions far more water-dispersible than those containing the aforementioned polyoxyethylene sorbitan monooleate alone as the sole dispersing agents for this purpose.

In accordance with the process employed for preparing these compositions, the oil soluble vitamin is blended with the polyethylene glycol 400 monooleate or other ester as specified above, followed by the addition of polyoxyethylene sorbitan monooleate. This preparation is mixed mechanically until it is homogeneous. This formulation is then added to ice water and mixed until it is well dispersed; the time required being usually less than one minute.

Alternatively the oil soluble vitamin may be blended together with corn oil or other mineral or vegetable oil, followed by the addition of the ester and finally by the addition of polyoxyethylene sorbitan monooleate. This preparation is also readily dispersed in water. Care must be taken during the course of these operations to ensure that aeration of the mixture does not occur as this will tend to have a deleterious effect upon the vitamin component caused by oxidative degradation of the same. Upon completion of this step, conventional sweetening and flavoring agents, as well as preservatives like methyl and propyl paraben, antioxidants such as ethoxyquin, feed supplements such as molasses, urea and phosphoric acid, or antibiotics such as oxytetracycline or neomycin can be added to the mixture at this point to afford the desired product in finished dosage form.

The compositions prepared according to the present invention have all been found to be stable (as regards potency) for periods of up to 2 weeks at temperatures ranging as high as 56°C., as well as for periods of up to 26 weeks when tested at room temperature. Furthermore, stability testing in aqueous dispersion shows the present compositions to be at least as stable as those obtained with the commercial combinations of the prior art which contain only the polysorbate component alone as the sole dispersing agent in each case. On the other hand, the use of such agents as glycerin, propylene glycol and ethyl acetate in place of the polyethylene glycol component of the present compositions tends to cause unsatisfactory results as these compositions were all found to be inferior by reason of immiscibility, poor vitamin stability, or unsatisfactory dispersion characteristics.

The following examples are illustrative in nature and are not to be construed as limiting the invention, the scope of which is defined by the appended claims.

EXAMPLE I

A stable, readily ice-water dispersible multivitamin A, $D_2$ and E oil soluble composition was prepared by blending together:

| VO 4276-181 | | |
|---|---|---|
| Vitamin A Palmitate | 560.5 | grams |
| Vitamin $D_3$ resin concentrate 25 MU/gr. | 9.44 | grams |
| Vitamin E Acetate 92% concentrate | 455. | grams |
| Ethoxyquin (antioxidant) | 120. | grams |
| Polyoxyethylene sorbitan monooleate | 300. | grams |
| Polyethylene glycol 400 monooleate | 550. | grams |

This was accomplished by blending the oil soluble vitamins with polyethylene glycol 400 monooleate followed by the addition of polyoxyethylene sorbitan monooleate. The final preparation was mixed with an ordinary low-powered motor stirrer until homogeneous. One gram of this preparation containing 400,000 units/gram of Vitamin A, 100,000 units/gram Vitamin $D_2$, and 200 units/gram Vitamin E was added to four liters of ice water and gently stirred with a small magnetic stirring bar. The formulation was quickly dispersed in less than one minute where a similar purchased formulation required many hours to disperse.

A particularly useful composition of this invention illustrating a preferred embodiment of same is one consisting essentially of up to 28% (509,600 units/gram) Vitamin A palmitate, up to 2% Vitamin $D_2$ concentrate (500,000 units/gram), and up to 20% Vitamin E acetate (200 l. units/gram), blended with 30% polyethylene glycol 400 monooleate, 18% polyoxyethylene sorbitan monooleate, and stabilized against oxidation and polymerization with 2% Ethoxyquin. (1,2 dihydro-6-ethoxy-2,2,4-trimethylquinoline). In cases where a lower potency product is required, the missing weight may be substituted with a low viscosity vegetable oil or preferably with a glycerol or propylene glycol ester of low molecular weight fatty ester with 8-14 carbon atoms.

EXAMPLE II

Another example of this useful composition was prepared by blending together:

| VO 4276-226 | | |
|---|---|---|
| Vitamin A Palmitate concentrate 1.02MU/gram | 18.3 | grams |
| Vitamin $D_2$ 40 MU/gram crystalline Calciferol | 0.13 | grams |
| Vitamin E Acetate concentrate 94.2% activity | 19.6 | grams |
| Corn oil | 8.21 | grams |
| Polyoxyethylene sorbitan monooleate | 20. | grams |
| Polyethylene glycol 400 monooleate | 32. | grams |
| Ethoxyquin | 1.76 | grams |

This was accomplished by blending together the oil soluble vitamins with polyethylene glycol 400 monooleate followed by the addition of polyoxyethylene sorbitan monooleate. The final preparation was mixed by an ordinary low powered laboratory motor stirrer until homogeneous. The formulation was fluid at 0°C., and readily dispersible into ice water within several minutes of slow stirring.

EXAMPLE III

Another example of this useful composition was prepared by blending together:

| VO 4276-211B | | |
|---|---|---|
| Vit. A. Palmitate pure 1.74 Mu/gram | 400 | grams |
| Vit. $D_3$ resin concentrate 27.4 MU/gram | 51.0 | grams |
| Vit. E Acetate concentrate 94.2% activity | 82.0 | grams |
| Ethoxyquin antioxidant | 20. | grams |
| Corn oil | 477.0 | grams |

| VO 4276-211B | | |
|---|---|---|
| Polyethylene glycol monooleate | 660. | grams |
| Polyoxyethylene sorbitan monooleate | 340. | grams |

This was accomplished by blending together corn oil with the oil soluble vitamins followed by the addition of polyethylene glycol 400 monooleate, and finally with the addition of Polyoxyethylene sorbitan monooleate. One pound of this formulation contained 249,000,000 units of Vitamin A palmitate, 269,000,000 units of vitamin $D_3$, 16,700 units of Vitamin E Acetate and 0.16 oz. of Ethoxyquin as an antioxidant. One gram of this formulation was dispersed into 10 ml. of tap water and aged in a loosely stoppered 250 ml. flask for 10 days at 56°C. The Vitamin A Palmitate had a retention of 72% indicating a high degree of stability in aqueous dispersions at room temperature for an extended period of time. This procedure was repeated using molasses, urea, and phosphoric acid liquid feed supplement with equivalent results.

EXAMPLE IV

Another example of this useful composition was prepared by blending together:

| VO 4276-210 | | |
|---|---|---|
| Vit. A Acetate Concentrate 1.598 MU/gram | 219 | grams |
| Vit. $D_3$ resin concentrate 27.4 MU/gram | 25.5 | grams |
| Vit. E Acetate concentrate 94.2% activity | 41. | grams |
| Ethoxyquin | 33. | grams |
| Corn oil | 150 | grams |
| Polyethylene glycol 400 monooleate | 281.5 | grams |
| Polyoxyethylene sorbitan monooleate | 250. | grams |

This was accomplished by blending together corn oil with oil soluble vitamins followed by the addition of polyethylene glycol 400 monooleate and finally with the addition of polyoxyethylene sorbitan monooleate and Ethoxyquin. One pound of this formulation contained 149,000,000 units of Vitamin A Acetate, 269,000,000 units of Vit. $D_3$, and 16,700 units of Vitamin E. One gram of this formulation was dispersed in 10 ml. of tap water and aged in a loosely stoppered 250 ml. flask for 10 days at 56°C. The Vitamin A Acetate had a retention of 81% indicating a high degree of stability in aqueous dispersion at room temperature for an extended period of time.

EXAMPLE V

Another example of this useful composition was prepared by blending together:

| Vitamin E Acetate 100% activity | 300 grams |
|---|---|
| Neobee M-20 propylene glycol esters of $C_8$ to $C_{14}$ fatty acids (Drew Chem. Co.) | 200 grams |
| Ethoxyquin | 10 grams |
| Polyethylene glycol 400 monooleate | 300 grams |
| Polyoxyethylene sorbitan monooleate | 190 grams |

This was accomplished by blending together tocopherol acetate with a modified vegetable oil (Neobee M-20) followed by the addition of polyethylene glycol 400 monooleate and finally with the addition of polyoxyethylene sorbitan monooleate and Ethoxyquin. The final preparation was mixed by an ordinary low powered laboratory motor stirrer until homogeneous. One pound of the final preparation mixed with molasses, urea, and phosphoric acid liquid feed supplement was sufficient to supplement the Vitamin E requirement for approximately 1,500 full grown cattle.

EXAMPLE VI

Another example of this useful composition was prepared by blending together:

| VO 4276-184 | | |
|---|---|---|
| Vitamin A Concentrate 1.16 MU/gram | 275.1 | grams |
| Ethoxyquin | 18 | grams |
| Polyethylene glycol 400 monooleate | 60.9 | grams |
| Polyoxyethylene sorbitan monooleate | 146 | grams |

This was accomplished by blending together Vitamin A Acetate concentrate and ethoxyquin with polyethylene glycol 400 monooleate followed by the addition of polyoxyethylene sorbitan monooleate. One gram of this formulation containing 600,000 units of Vitamin A was dispersed into 10 ml. of tap water and aged in a loosely stoppered 250 ml. flask at 56°C. for 10 days. The Vitamin A acetate had a retention of 73% indicating a high degree of aqueous stability. One gram of this formulation was dispersed into 10 ml. of molasses, urea, and phosphoric acid liquid feed supplement and aged for 10 days in a loosely stoppered 250 ml. flask at 56°C. The Vitamin A Acetate had a retention of 82% indicating a high degree of aqueous stability at room temperature for an extended period of time.

EXAMPLE VII

Another example of this useful composition was prepared by blending together:

| VO 4276-184 | | |
|---|---|---|
| Vit. A. Acetate Concentrate 1.16 MU/gram | 275.1 | grams |
| Ethoxyquin | 18. | grams |
| Polyethylene glycol 400 monooleate | 60.9 | grams |
| Polyoxyethylene sorbitan monooleate | 146. | grams |

This was accomplished by blending together Vitamin A Acetate concentrate and ethoxyquin with polyethylene glycol 400 monooleate followed by the addition of polyoxyethylene sorbitan monooleate. One gram of this formulation containing 600,000 units of Vitamin A was dispersed into 10 ml. of tap water and aged in a loosely stoppered 250 ml. flask at 56°C. for 10 days. The Vitamin A acetate had a retention of 73% indicating a high degree of aqueous stability. One gram of this formulation was dispersed into 10 ml. of molasses, urea, and phosphoric acid liquid feed supplement and aged for 10 days in a loosely stoppered 250 ml. flask at 56°C. The Vitamin A Acetate had a retention of 82% indicating a high degree of aqueous stability at room temperature for an extended period of time.

EXAMPLE VIII

Another example of this useful composition was prepared by blending together:

| VO 4276-209x | | |
|---|---|---|
| Vit. A Palmitate pure 1.75 MU/gram | 200 | grams |
| Vit. $D_3$ resin concentrate 27.4 MU/gram | 25.5 | grams |
| Vit. E Acetate concentrate 94.2% activity | 41. | grams |
| Ethoxyquin antioxidant | 33. | grams |

-continued

VO 4276-209x

| | | |
|---|---|---|
| Neobee M-20 propylene glycol esters of C$_8$ to C$_{14}$ fatty acids (Drew Chem. Co.) | 200.5 | grams |
| Decaglycerol tetra oleate | 330. | grams |
| Polyoxyethylene sorbitan monooleate | 170. | grams |

This was accomplished by blending together the oil soluble vitamins with Neobee M-20 followed by the addition of Ethoxyquin and decaglycerol tetraoleate, and finally with the addition of polyoxyethylene sorbitan monooleate. One pound of the final formulation contained 150,000,000 units of Vitamin A, 269,000,000 units of Vitamin D$_3$ and 16,700 units of Vitamin E. One pound of the final formulation when mixed with molasses, urea and phosphoric acid liquid feed supplement was sufficient to supplement the Vitamin A and D daily requirement for more than 1,500 full-grown cattle.

EXAMPLE IX

A stable, readily ice-water dispersible multivitamin A, D$_2$ and E, neomycin-oxytetracycline, non-aqueous formulation was prepared by blending together:

VO 4276-200D

| | | |
|---|---|---|
| Calf Starter Formulation: | | |
| Oxytetracycline crude concentrate 550 units/mg. activity | 436 | grams |
| Neomycin sulfate | 369 | grams |
| Vit. A Acetate conc. 2.0 MU/gr. | 530 | grams |
| Ethoxyquin | 50 | grams |
| Vit. E Acetate 92.4% activity | 57 | grams |
| Polyethylene glycol 400 monooleate | 2770 | grams |
| Polyoxyethylene sorbitan monooleate | 1500 | grams |
| Polyethylene glycol 400 (to adjust potency) approx. | 5000 | grams |

This was accomplished by blending together micronized oxytetracycline crude concentrate and neomycin sulfate with the oil soluble vitamins and ethoxyquin followed with the addition of polyethylene glycol 400 monooleate, followed with the addition of polyoxyethylene sorbitan monooleate, and the final formulation was adjusted to standard weight with polyethylene glycol 400. The final preparation was mixed with an ordinary low powered laboratory motor stirrer until homogeneous. Eleven and one half grams of approximately ½ teaspoon of the final formulations contains 500,000 units of Vitamin A, 50,000 units of Vitamin D$_2$, 50 units of Vitamin E, 220 mg. of terramycin, and 220 mg. of neomycin base, or one therapeutic dose. A half teaspoon of the formulation readily dispersed into 1 gallon of calf drinking water or milk. Vitamin A and the antibiotics had a retention of 95+% after 6 months at room temperature.

EXAMPLE X

A stable readily ice water dispersible multivitamin A, D$_2$ and E oil soluble composition which has valuable cold flow properties was prepared by blending together:

| | | |
|---|---|---|
| Vitamin A Concentrate 1.78M/gr. | 23.7 | grams |
| Vitamin D$_2$ resin concentrate 25M/gr. | 0.9 | grams |
| Vitamin E Acetate Concentrate 93% purity | 11.3 | grams |
| Ethoxyquin | 4 | grams |
| Polyoxyethylene sorbitan monooleate | 20 | grams |
| Vegetable oil M-20 | 20 | grams |
| Polyethylene glycol 400 monooleate | 15.1 | grams |
| Ethanol | 5.0 | grams |

This was accomplished by blending the oil soluble vitamins with vegetable oil and polyethylene glycol 400 monooleate followed by the addition of polyoxyethylene sorbitan monooleate, Ethoxyquin, and normal propanol. The final preparation was mixed with an ordinary low powered laboratory motor stirrer until homogeneous. The formulation was chilled to 0°F. for several hours. One teaspoon of the formulation was poured into a 3 gallon pail of ice water with moderate stirring for 1 minute. The formulation was quickly dispersed. Comparable results are obtained if an identical amount of normal propanol is substituted for the ethanol of this formulation.

What we claim is:

1. A pharmaceutical composition for aqueous dispersion to give clear, stable solutions of vitamins consisting essentially of from about 25% to about 55%, by weight of the total composition, of oil-soluble vitamin A, vitamin D$_2$, vitamin D$_3$, vitamin E, or combinations thereof together with from about 35% to about 85%, by weight of the total composition, of a dispersing agent consisting essentially of polyoxyethylene sorbitan monooleate having about 20 oxyethylene units per molecule plus an ester selected from polyethylene glycol 400 monooleate, decaglycerol dioleate, and decaglycerol tetraoleate, the ratio of said sorbitan monooleate to said ester being from about 3:1 to about 1:3.

2. The composition of claim 1 wherein the ratio of said polyoxyethylene sorbitan monooleate to said ester is from about 2:1 to about 1:2.

* * * * *